US00PP08906P

United States Patent [19]

Drewlow

[11] Patent Number: Plant 8,906

[45] Date of Patent: Sep. 20, 1994

[54] IMPATIENS PLANT NAMED SONATA

[75] Inventor: Lyndon W. Drewlow, Ashtabula, Ohio

[73] Assignee: Mikkelsens, Inc., Ashtabula, Ohio

[21] Appl. No.: 163,765

[22] Filed: Dec. 9, 1993

[51] Int. Cl.[5] ..... A01H 5/00
[52] U.S. Cl. ..... Plt./87.6
[58] Field of Search ..... Plt. 87.6

*Primary Examiner*—James R. Feyrer
*Attorney, Agent, or Firm*—Foley & Lardner

[57] ABSTRACT

A new and distinct cultivar of Impatiens plant named Sonata, characterized by its double flower form with ten petals, salmon-orange flower color, relative small diameter flowers carried on green pedicels, long solid deep green leaves, later flowering habit due to double flower form; upright, highly self-branching and floriferous habits, tolerance to both high and cool temperatures, and its adaptability to be grown in 10 cm up to 15–25 cm containers.

2 Drawing Sheets

The present invention relates to a new and distinctive cultivar of Impatiens plant, botanically known as Impatiens, commercially known as New Guinea Impatiens, and known by the cultivar name Sonata.

The new culture was developed in a controlled breeding program conducted by the inventor Lyndon W. Drewlow in Ashtabula, Ohio. Sonata was created by crossing Mikkelsen Seedling No. 90-138-2 (seed parent) with Mikkelsen Seedling No. 90-141-1 (pollen parent). Both parents are proprietary cultivars used in the breeding program.

Asexual reproduction by terminal or stem cuttings carried out by or under the supervision of the inventor at Ashtabula, Ohio has shown that the unique features of this new Impatiens are stabilized and are reproduced true to type in successive propagations.

The following combination of characteristics distinguish the new Impatiens from both its parent varieties and other cultivated Impatiens of this type known and used in the floriculture industry. The description includes reference to comparison cultivars Zenith, disclosed in U.S. Plant Pat. No. 5,804, and Allegro, disclosed in a pending application of the inventor.

1. Sonata is a representative of an entirely new class of New Guinea Impatiens that have 10 flower petals, double the number of petals of the single flower type such as Zenith. Allegro is another cultivar in the double-flowered group.

2. Sonata has a salmon-orange flower color (34B-C) while Zenith is a deeper salmon orange (40A).

3. Sonata has a smaller diameter flower (5.5 to 6.0 cm) than Zenith which has a diameter of 6.0 to 7.0 cm. Allegro is similar in flower diameter to Sonata.

4. Sonata has green flower pedicels as does Allegro, with Zenith having a flower pedicel with a reddish cast.

5. Sonata has a solid green leaf while Allegro and Zenith have cream variegation around the midrib of the leaf, with Zenith having much more cream variegation than Allegro.

6. Mature leaves of Sonata are 10–11 cm long and 3.5 to 4.0 cm wide, longer and slightly broader than the leaves of Zenith (6.5 to 7.5 cm long and 2.5 to 3.0 cm wide) and Allegro (7.0 to 8.0 cm long and 3.0 to 3.5 wide).

7. Sonata is 3 to 5 days later to bloom than Zenith as it takes the double flower with 10 petals longer to develop and open than the 5 petals of the single flowers of Zenith. Allegro is similar in bloom date to Sonata.

8. Both Sonata and Allegro have a large area of green around the midrib on the backside of the standard petal on the lower whorl of petals, while Zenith has only a trace of green coloration on the midrib itself.

9. Sonata has a more upright growth habit and height (24–26 cm), compared to both Zenith and Allegro which are more mounded and compact, and 18 to 20 cm in height.

10. Sonata is much more self-branched than Zenith with Allegro being similar to Sonata in degree of self-branching.

In the photographic drawings, the color photo at the top illustrates in perspective view the overall appearance of Sonata, with the colors being as true as it is reasonably possible to obtain in a color reproduction of this type. The color photo was taken on Oct. 8, 1993 under natural light under 40% saran in a shaded glass greenhouse in Ashtabula, Ohio on a cloudy day. The black and white photo on the bottom shows three (3) views of a typical flower of the new cultivar.

The following is a detailed description of Sonata, based on plants produced in greenhouses in Ashtabula, Ohio during the summer season of the year. Plants were grown in 15 cm pots and measurements were taken 18 weeks after rooted cuttings were planted. Height measurements were taken from the soil line of the container. The plants were grown at 65°–68° F. night temperatures under 3000–4000 foot candles of light, and 250 ppm nitrogen, 75 ppm potassium, and 250 ppm phosphorous nutritional levels, with trace elements added. The habit of growth, foliage coloration, leaf variegation, size of leaves and flower size will be influenced by nutritional and environmental conditions, without, however, any variance in the genotype.

Color references are made to The Royal Horticultural Society Colour Chart except where general terms of ordinary dictionary significance are used.

Parentage: A controlled cross between female parent Mikkelsen Seedling No. 90-138-2 and male parent Mikkelsen Seedling No. 90-141-1.

Propagation:

(A) *Type cutting.*—Stem cuttings 15 mm long will develop 4 to 5 cm long in 18 to 21 days.

(B) *Time to root.*—8–10 days at 23° C. summer; 10–12 days at 20° C. winter.

(C) *Rooting habit.*—Heavy, fibrous.

Plant description:

(A) *Form and habit of growth.*—Semi-upright, spreading; intermediate in height, flowers at the top of leaf canopy; continuous flowering; vigorous growing herb.

(B) *Foliage description.*—Dark green with yellow-green midribs; no variegation. (1) Size: 10 to 11 cm long and 3.5 to 4.0 cm wide for average mature leaf. (2) Shape: Lanceolate with acuminate apex and acute base. (3) Texture: Glabrous upper and lower leaf surfaces. (4) Margin: Finely serrated with fine ciliate. (5) Color: Young foliage, top side is 146A; under side is 146B; mature foliage, top side is 147A; under side is 147B. (6) Veination: Pinnate, green in color.

Flowering description:

(A) *Flowering habit.*—Flowering is continuous from leaf whorl in a progressively orderly manner with one flower per leaf axil. When the last flower in a leaf whorl opens the first flower in the leaf whorl above starts to open. It takes 5 to 7 days for a mature bud to fully open and the flower may last two weeks or longer depending on environment.

(B) *Natural flowering season.*—Indeterminant and continuous, quantity of flowering increases with increasing levels of light.

(C) *Flower buds.*—Ellipsoidal, flowers perfect; light reddish purple cast to 4.5 cm long spur with green tip on mature bud, with throat behind the ovary and originating from the major sepal.

(D) *Flowers borne.*—On individual green pedicels 3.0 to 3.5 cm long from whorl of 6 to 7 leaves, flowering progressively around the whorl as buds and leaves develop. One flower per leaf axil is normal.

(E) *Quantity of flowers.*—Floriferous because of self-branching nature of plant, number of leaves in each whorl, long lasting flowers, and full appearance of double flowers.

(F) *Diameter of flower.*—5.5 to 6.0 cm.

(G) *Petals.*—(1) Shape: Heart-shaped; keel petals of bottom whorl of petals are the largest. (2) Color: Top side in summer when opening is 34B to 34C, fading to 34D; under side is 34C. (3) Number of petals: Ten (10). (4) Type of petals: Only one true standard petal in lower whorl; upper whorl petal in standard position is more keel-like; two sets of wing petals; two sets of keel petals plus the keel-like petal in upper whorl.

(H) *Reproductive organs.*—(1) Stamens: Five (5) in number. (a) Anther: hooded shape; color is cream with a slight reddish tint on top of hood. (b) Pollen color: Cream. (2) Pistils: (a) Stigma shape: Five (5), segmented column; color is greenish white. (b) Style color: Greenish white. (c) Ovaries: Five (5) in number; size is 6 mm when mature; color is green.

Disease resistance: No significant disease or insect problems to date.

OTHER IMPORTANT CHARACTERISTICS

1. Self-branching characteristic and semi-upright, spreading intermediate height make Sonata suitable for 10 cm pot production, but Sonata is vigorous enough for 15 and 25 cm pot production as well.
2. Sonata can withstand both high temperatures and sunlight as well as low temperatures (40° to 50° F.), thus extending the outside growing season as well as the locations where Sonata can be planted.
3. The ten (10) flower petals result in a fuller flower as compared to the normal five (5) petals. A double flowered plant with the same number of flowers as a single flowered plant will appear substantially more colorful.

I claim:

1. A new and distinct cultivar of Impatiens plant named Sonata, as illustrated and described.

* * * * *

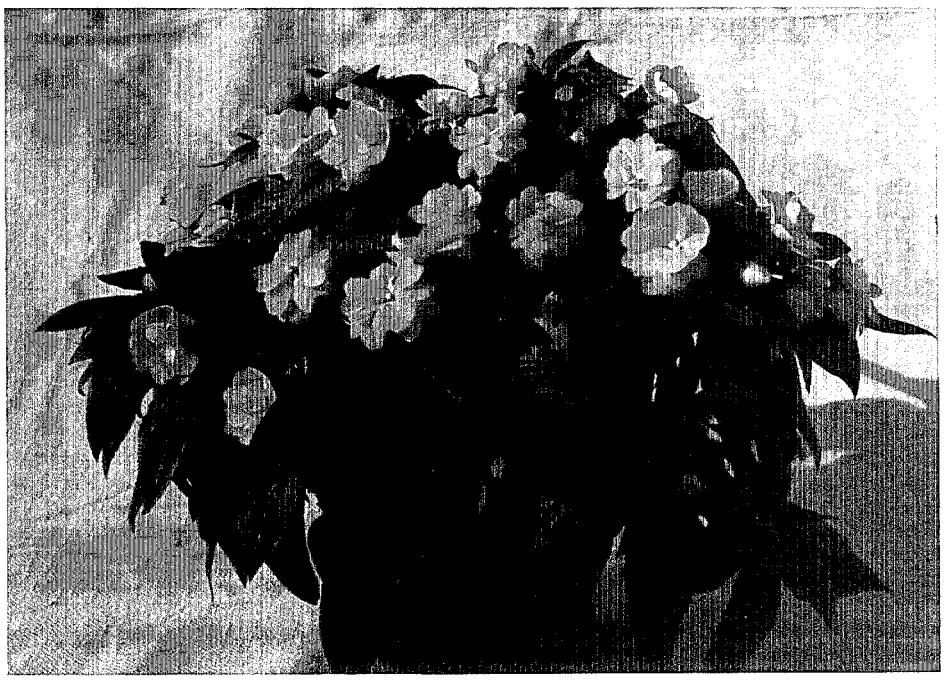

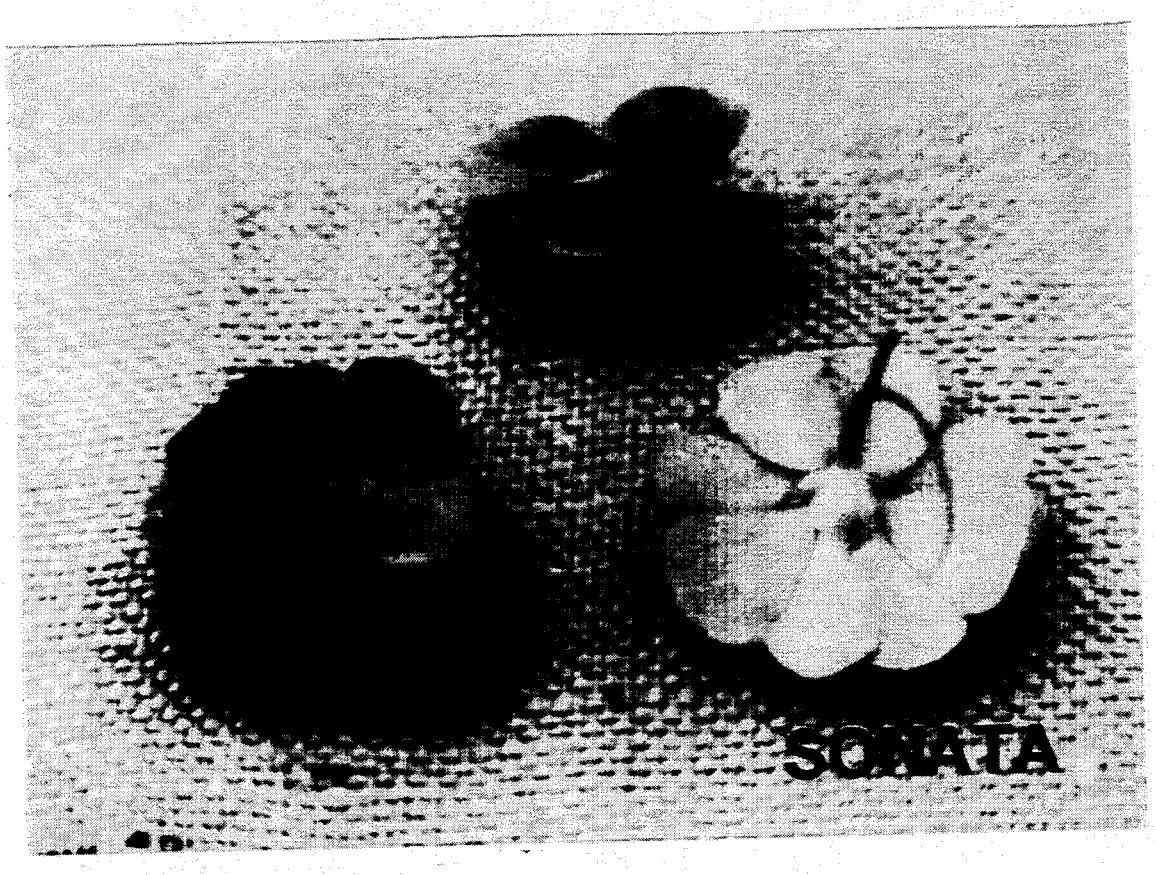
SONATA